United States Patent
Kay

(10) Patent No.: US 7,189,251 B2
(45) Date of Patent: Mar. 13, 2007

(54) OPEN HELICAL ORGANIC TISSUE ANCHOR HAVING RECESSIBLE HEAD AND METHOD OF MAKING THE ORGANIC TISSUE ANCHOR

(75) Inventor: David B. Kay, Akron, OH (US)

(73) Assignee: Orthohelix Surgical Designs, Inc., Akron, OH (US)

(*) Notice: Subject to any disclaimer, the term of this patent is extended or adjusted under 35 U.S.C. 154(b) by 380 days.

(21) Appl. No.: 10/446,768

(22) Filed: May 28, 2003

(65) Prior Publication Data

US 2003/0229350 A1 Dec. 11, 2003

Related U.S. Application Data

(63) Continuation-in-part of application No. 10/089,105, filed on Feb. 19, 1998, which is a continuation-in-part of application No. 08/517,259, filed on Aug. 23, 2005, now Pat. No. 5,662,683.

(51) Int. Cl.
*A61B 17/04* (2006.01)

(52) U.S. Cl. .......................... 606/232; 606/60; 606/72; 606/73; 606/218; 411/395; 470/6; 470/8; 470/10; 470/14; 470/19

(58) Field of Classification Search .................. 606/60, 606/65, 66, 72, 73, 151–153, 155, 218, 232; 411/395, 425, 43, 530, 929.1; 470/6, 8, 10, 470/11, 12, 14, 27, 29
See application file for complete search history.

(56) References Cited

U.S. PATENT DOCUMENTS

| | | | | | |
|---|---|---|---|---|---|
| 4,762,453 | A | * | 8/1988 | DeCaro | 411/383 |
| 5,443,509 | A | * | 8/1995 | Boucher et al. | 606/60 |
| 5,582,616 | A | * | 12/1996 | Bolduc et al. | 606/143 |
| 5,626,613 | A | * | 5/1997 | Schmieding | 606/232 |
| 5,662,683 | A | * | 9/1997 | Kay | 606/232 |
| 5,824,008 | A | * | 10/1998 | Bolduc et al. | 606/143 |
| 5,904,696 | A | * | 5/1999 | Rosenman | 606/151 |
| 6,045,554 | A | * | 4/2000 | Grooms et al. | 606/73 |
| 6,468,309 | B1 | * | 10/2002 | Lieberman | 623/17.11 |

* cited by examiner

*Primary Examiner*—Michael J. Hayes
*Assistant Examiner*—Michael G Mendoza
(74) *Attorney, Agent, or Firm*—Hudak, Shunk & Farine Co. LPA

(57) ABSTRACT

The invention relates to a tissue anchor which is an open helix of biocompatible material having a slope of from 0.5 to 10 turns per centimeter, a length from 3 to 75 millimeters, a diameter of from 1.5 to 11 millimeters, and an aspect ratio of from about 3 to about 5 to 1. The anchor can have a head which is capable of securing or clamping tissue together, such as holding a suture to secure a ligament or tendon to bone. The anchor can also have a head which causes an inward, compressive loading for use in fastening bone to bone, orthopedic plates to bone, or cartilage to bone. The head may be an integral member and may include a self-reinforcing wedge which joins the helix to the head. Further, the elongate member, or filament that forms the helix may have a tapering diameter along its length.

21 Claims, 3 Drawing Sheets

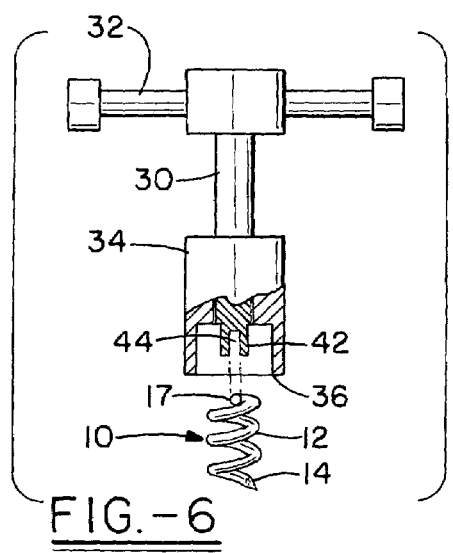
FIG.-6
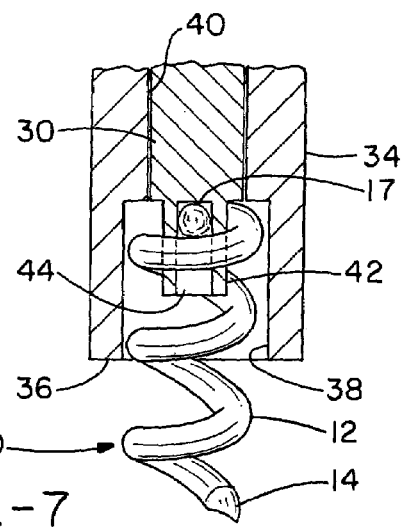
FIG.-7
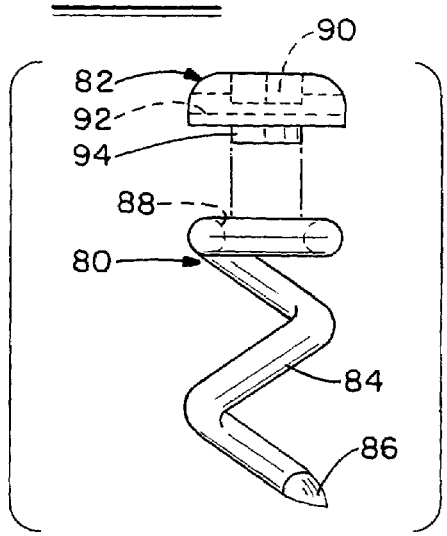
FIG.-8
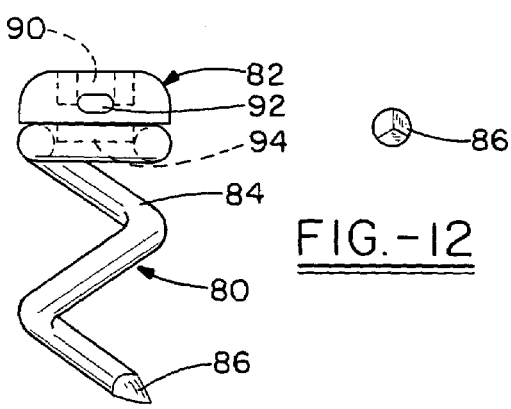
FIG.-11
FIG.-12
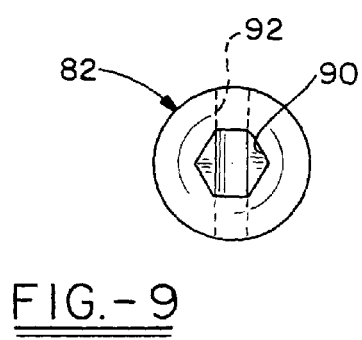
FIG.-9
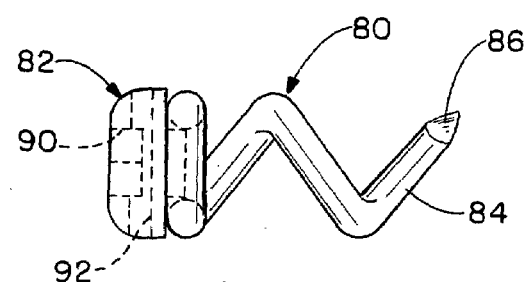
FIG.-10

OPEN HELICAL ORGANIC TISSUE ANCHOR HAVING RECESSIBLE HEAD AND METHOD OF MAKING THE ORGANIC TISSUE ANCHOR

CROSS REFERENCE

This is a Continuation-In-Part application of U.S. application based on PCT10/089,105, filed Feb. 19, 1998, which is in turn a Continuation-In-Part application of U.S. Ser. No. 08/517,259, filed Aug. 23, 1995 for OPEN HELICAL ORGANIC TISSUE ANCHOR AND METHOD OF FACILITATING HEALING now U.S. Pat. No. 5,662,683.

FIELD OF THE INVENTION

The present invention relates to tissue anchors as well as to methods of promoting healing or repairing hard or soft, living, organic tissue using an open helical anchor. Further, the invention relates to a method of making the tissue anchor. In a further embodiment, the helical anchor comprises a filament which has a taper along its longitudinal length.

BACKGROUND OF THE INVENTION

The present invention relates to an anchor (or connector) which can be used to fasten organic tissue in close proximity in order to afford the tissue the opportunity to heal. The anchor of the present invention can be used to anchor and clamp dense, regular and/or dense, irregular connective tissue in place in relation to bone. The anchor can also be used for tissue transplants, i.e., for holding tissue in fixed relation to bone, and can also be used in bone as a buttress, such as for buttress plating techniques, or to fasten pieces of bone together as a screw substitute. Further, the anchor can be used in soft tissue applications. Thus, as used herein "tissue anchor" relates broadly to the invention used as a screw, clamp, or anchor in the narrow sense of the word which holds organic tissue, i.e. bone to bone, soft tissue to bone, or soft tissue to soft tissue.

As compared to the prior art, the anchor of the present invention allows a method of holding together organic tissue with minimal disruption to the biological environment or to the tissue itself. For example, prior art devices and methods customarily require a large hole for insertion of the anchoring device, causing not only structural damage to the implantation site, but also inflicting further trauma to the biological site such as generating heat, introducing further possibility for infection, and destroying bone which may be needed to help heal the repaired area. Such trauma is amplified in cases where prior art devices malfunction during the implant procedure. Hooks or screws can get stuck and further obscure the operating site or require tedious removal.

The anchor of the present invention may be very useful for applications such as anchoring ligaments or tendons when performing soft tissue surgical reconstruction, rupture tendons, or torn ligaments, in which the surgeon wants to reconstruct or repair connective tissue with respect to the bone or with respect to other soft tissue.

The anchor device functions to hold together the tissue (such as connective tissue to bone) for a relatively limited time frame e.g., six to twenty-six weeks, during which time the biological system will heal.

The anchor of the present invention can be used with advantage in many of the same applications in which cancellous screws are used in addition to applications in which traditional prior art anchoring techniques are unsatisfactory. The anchor of the present invention is far less invasive to implant than cancellous screws or hook-style anchors, i.e., the implant has a minimized mass, the insertion point is small relative to the size of the implant, and the device involves minimal removal of native tissue. In addition, the area of bone or other tissue which is needed to secure the present invention can be of poorer quality than for prior art devices.

Additionally, the anchor of the present invention can be removed and minimally reangulated in order to utilize the same surgical site. Prior art devices require a large hole (relative to implant size) to be drilled in order to implant the device, and once the hole is contaminated by malfunction or misalignment of the device, it is necessary to drill another hole far enough away to achieve stability in a new location. Given the surgical context, this is extremely inconvenient.

The anchor of the present invention can be used in methods of ligament, tendon, or other tissue repair. For example, the anchor can be used for a method involving cartilage transplant and it can be used alone or in conjunction with a plate for a method of buttressing bone where the quality of bone may be questionable due to trauma or degenerative disease. The anchor may be used in methods of fixation involving connective tissue repair and replacement and may be inserted using a plunge-handle or "T" handle inserter which utilizes longitudinal travel in order to achieve rotational insertion. The handle and insertion tool may be a standard screwdriver or a jig-outer cannula system for a hex head or headless helix, respectively.

Specifically, the anchor is used in a ligament or tendon in which a pilot hole, having a diameter much smaller than the outer diameter of the helical anchor, is drilled in the cortex of the bone. The angle of implantation can be varied as necessary. The anchor is subsequently mounted or loaded into the insertion tool, threaded into the pilot hole, and screwed into the bone an appropriate distance so that the anchor head can be accessed but is not obtrusive. The ligament or tendon is attached to the anchor, such as by suturing.

In addition, the anchor of the present invention can be used to anchor plates and is particularly useful in instances where the bone is of poor quality. The head can be a bend in the wire which forms a cross bar and which can be implanted using a slotted instrument. A particularly desirable head for some applications has an internal hex slot to permit the anchor to be implanted. In addition, the head has a transverse through slot to hold a suture. The head has a low, rounded profile with a distal stem which fits inside a ring of the helix and is laser-welded thereto. In an alternative embodiment, the anchor has a solid cylindrical head which extends from the spiral and has the same outer diameter. This head also has an internal torque receiving hexagon, which has a hole in the center of the bottom surface of the hex shaped recess. This hole allows for cannulation for implantation. Further, the head has a hole (or more precisely, two aligned holes), in a direction transverse to the longitudinal axis of the spiral to allow a suture to be attached to the head. For the screw used with a plate, the screw may have a head with a diameter that exceeds the diameter of the helix, or a conical washer may be used which allows for angulation of the head in the plate, or the head may include external threads that mate with internal threads in the plate. In an alternative embodiment, the head comprises a rivet or clamp, which can be fixed to a boss formed at the top of the helical structure. This version of the anchor can be driven into bone using matching Male-Female head.

Moreover, in accordance with an aspect of the invention, the structure is made by forming a screw type blank having an externally threaded member which extends from a cylindrical head having an internal torque receiving recess, preferably a hexagon. The blank is subsequently drilled internally to form an open helical structure attached to the solid head. The material removed is tapered along the long axis decreasing in the direction of the top of the helical structure where the apex of the cone is at the proximal position of the helix. This places more material at the driver level where the helix joins the head and takes the driving torque. The conical opening may still include a through hole for cannulation. In addition, it has been found to be an advantage for the helix to include a taper from the insertion end toward the head in the direction of the longitudinal length of the filament. This provides for significantly higher test results in the pull-out strength.

SUMMARY OF THE INVENTION

The anchor in accordance with the invention comprises an open helical structure which is a constant or varied-diameter, elongate member, fiber, filament or thread comprised of a relatively rigid, biocompatible material such as a wire having a diameter which may vary optimally from about 0.2 millimeters to about 5.0 millimeters. The length of the anchor will depend upon the particular application, but will range generally from about 3.0 millimeters to about 75.0 millimeters with the upper ranges being useful for buttressing techniques. The outer diameter of the helix will also vary in accordance with the application, but it will range generally from about 1.5 millimeters to about 15.0 millimeters. A suitable rate of slope for the helix is from about 0.5 to about 10 turns per centimeter. The aspect ratio of the helix, which as used herein means the ratio of the helix outer diameter to the fiber diameter, is an important ratio in order to achieve the proper stiffness to enable insertion and to firmly seat in the bone; a suitable range is 3.5 to 4.5.

Advantageously, the anchor of the present invention involves relatively simple, cost-effective manufacturing processes. The present anchor is also less intimidating to doctors and patients than prior art devices and can be used with simple, straight-forward instrumentation. Finally, since the device is relatively noninvasive, several can advantageously be used together in instances where more than one prior art device could not be used. It is preferred, but not necessary, that the helical structure has a constant circular diameter and a constant slope (meaning the rate of turn per unit of longitudinal length). Likewise in another embodiment, it is preferred that the filament that comprises the helical structure does not have a constant circular cross-section, but rather has a taper which increases from the insertion tip to the head, and which can have a cross-section other than a circle, such as a modified triangle or a thread shape. The increase is an increase of up to about 100% of the initial diameter, with a preferred range being in the 10–50%, and a more preferred range being in the range of 15 to 30% with the optimal taper being bout 25%.

For its connective applications, the anchor includes an attachment head at one end which is suitable for securing the tissue or suture which is to be held. For example, in the case of a filamentary anchor, the anchor may have a hook, crossbar or eyelet. For applications in which the anchor secures material such as cartilage or a buttressing plate, the head may have a surface which is designed to distribute the load evenly over the material.

In a second embodiment, the anchor will have a modular head. For example, the helical anchoring portion may terminate at the superficial end in a post that will accommodate one of several head options. These head options may include a button, clamp, clip, snap, or rivet. At the other end, the anchor includes a cutting or self-tapping point. The head may be a solid cylindrical construction which is integral to and the same diameter as the helical structure in order that the head will countersink into the fastening surface. In other words, the anchor does not have a smaller diameter area or necked area which fastens the head to the helix, likewise, the head does not extend beyond the outer diameter of the helix like an upholstery button that would be apt to wind or unwind during implantation. An outer cannula may be needed to support the helix and retain rigidity as it is driven into the bone. For example, it is envisioned that the helix, when used as anchor, may be packaged in a translucent medical grade plastic cannula that allows support to the helix and visualization as it is being driven in. This is a disposable piece that is discarded after implantation of the helix.

In accordance with another embodiment of the invention, a buttressing system is provided which comprises a plate having at least two through bores which are each engaged by an open-helix anchor.

In accordance with a method of the present invention, an anchoring site is surgically accessed, the helical anchor is screwed into the anchoring site, and connective tissue is secured to the attachment head of the anchor.

In accordance with another method of the invention, a bone is buttressed by surgically accessing an implant site, aligning a plate having at least one aperture over the site, and securing the plate to the implant site by inserting an open-helix anchor through the aperture and into the implant site to anchor the plate with respect to the implant site.

In accordance with another embodiment of the invention, a method of making the anchor comprises making an externally threaded blank of a relatively constant outer diameter, and consequently reaming the blank to form an open helical structure. Preferably, the blank is reamed so as to cause a conical removal of material at the apex of the cone, proximate the join of the head and the helix. This places more material at the driver level and tapers the threads. This strengthens the helix at the driver for transmission of torque. The resulting wedge shape to the threads increases the anchoring into the bone.

DESCRIPTION OF THE DRAWINGS

FIGS. 6 and 7 illustrate the tool which may be used for inserting the anchor;

FIG. 8 is an elevational assembly of a second embodiment of the anchor having a modular head;

FIG. 9 is a top view of the head illustrating the slot in phantom,

FIG. 10 is a side view of the second embodiment of the anchor device in accordance with the invention;

FIG. 11 is an elevation view of the embodiment shown in FIG. 8 rotated 90°;

FIG. 12 is a bottom end view of the helix portion of the embodiment shown in FIG. 10;

DETAILED DESCRIPTION OF THE INVENTION

Figure 2:
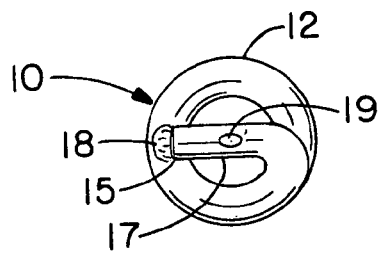
FIG. 2 is a top view taken of FIG. 1.
Figure 1:
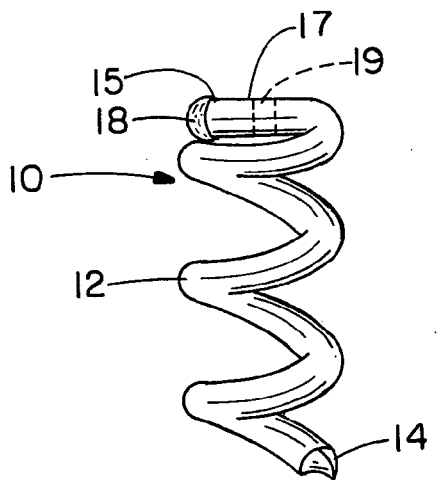
FIG. 1 is an elevational view of the anchor device showing the attachment head in side elevation.
Figure 3:
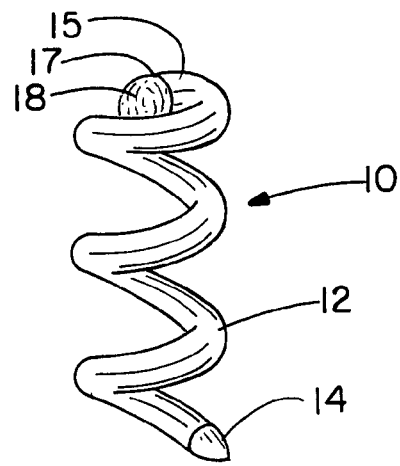
FIG. 3 is an elevational view similar to FIG. 1, but showing the anchor rotated 90° to the right so that the attachment head is seen in an end view.

In accordance with the invention, FIGS. 1–3 illustrates the anchoring device in accordance with the invention enlarged to show the invention in detail generally at 10. The anchoring device 10 comprises an open helix 12 having a pointed insertion tip 14 at one end and an attachment head 15 at the other end.

Preferably, the anchoring device is comprised of a rigid, biocompatible material having a high-yield strength such as stainless steel or titanium. The device can also be made from a biodegradable material such as polyglycolic acid ("PGA"), polylactic acid ("PLA"), polydiaxone hydroxy apatite ("PDA"), and the like. For example, the device 10 may be made from surgical-grade titanium or stainless steel wire having a wire diameter ranging from about 0.4 millimeters to about 3.0 millimeters, and more specifically from about 0.5 millimeters to about 2.0 millimeters, and most specifically from about 1.0 millimeters to about 2.0 millimeters. Optionally, the helix diameter may be of variable cross-section ranging from a smaller-diameter wire at the insertion tip to a larger-diameter wire near the attachment head 15.

The "slope" of the helix is used herein to mean the number of turns (i.e., one 360° rotation) per unit length and varies from about 0.5 turn per centimeter to about 10 turns per centimeter, and more specifically from about 0.5 turn to about 4 turns per centimeter, and most specifically from about 1 to about 2 turns per centimeter. The anchor generally comprises a length of helix sufficient to achieve from 0.75 to 4 complete 360° revolutions, or more specifically from about 1 to about 3 revolutions. Accordingly, the length of the anchor for most general fastening or anchoring applications is from about 3 to about 18 millimeters, and more specifically from about 4 to about 15 millimeters, and most specifically from about 8 to about 15 millimeters. For plating or buttressing applications, the length of the anchor will generally range from about 5 to about 75 millimeters, preferably from about 5 to about 40 millimeters and most preferably from about 10 to about 20 millimeters.

The overall outer diameter of the open helix portion 12 of the anchoring device 10, ranges from about 1.5 to about 11 millimeters, and more specifically from about 3 to about 9 millimeters, and most specifically from about 5 to about 7 millimeters. The wire is generally circular in cross-section, although it is envisioned that it may be angular such as diamond-shaped or rhombohedral. In accordance with an additional embodiment of the invention, the anchor has an integral head which has the same outer diameter as the helical structure. And further, the elongate member which forms the helix can have a generally triangular cross-section so that the overall impression is of a cutting thread with no core. It should however be noted that the open structure does not act like a screw in its performance, and in particular in the method of failure. In the embodiment shown in FIGS. 17–19, the filament has a taper in the diameter which decreases toward the insertion end. While this is shown as a circular cross-section, it can have the taper in alternative shapes, such a the triangular or thread-like shape. The taper represents a substantial improvement in the strength required.

It is important that the anchor have an aspect ratio of from about 3 to about 5, preferably from 3.5 to 4.5, and most preferably around 4. As used herein, aspect ratio means the ratio of the helix outer diameter to the wire diameter. If the ratio is too large, the device is too rigid, whereas if the ratio is too small, the device is overly flexible.

The attachment head 15 of the anchoring device 10 may vary according to the specific application. For example, it may be desirable to include a broader compression area for direct attachment of connective or soft tissue to bone, as compared to suture techniques involving suturing or wiring the soft tissue in place with respect to the anchoring device. Examples of attachment heads suitable for suturing or wiring connective tissue include crossbars, hooks and eyelets.

FIG. 1 illustrates an attachment head 15 having a crossbar 17 which arches slightly above the last helical turn and is attached such as by spot welding 18 at the terminal end. It may be further preferable to include an opening 19 or cannulation in the crossbar to allow for cannulated surgical techniques (i.e., placement of the anchor over a positioned wire which may be subsequently removed). The opening may range in size from 0.5 millimeters to 1.5 millimeters depending on the application.

Figure 4:
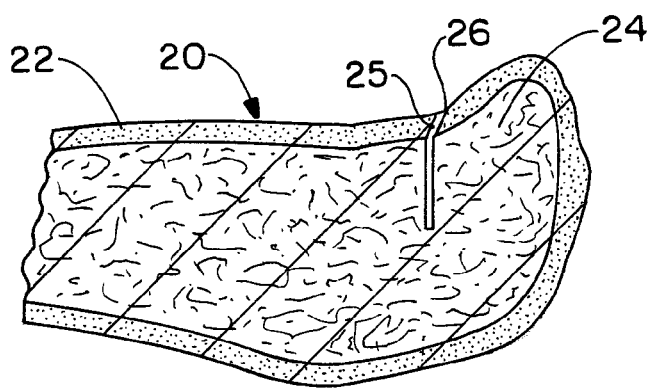
FIG. 4 illustrates the pilot hole in the bone prior to insertion of the anchor.
Figure 5:
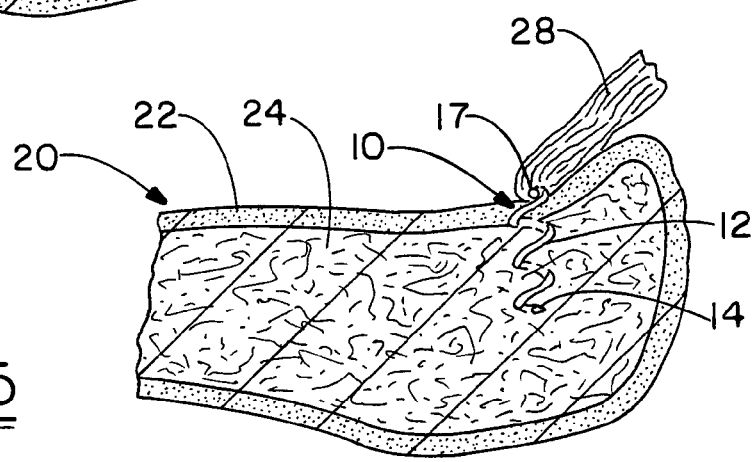
FIG. 5 illustrates an anchor in place in the cancellous portion of the bone with the attachment head projecting above the surface of the bone in order to allow attachment of the soft tissue to the anchor.

The device and method of the invention are illustrated in FIGS. 3–5. In particular, FIG. 4 illustrates a section of bone generally at 20 having a cortex 22 and a cancellous portion 24. A pilot hole 25 has been drilled in the cortex 22 in order to ease insertion of the anchoring device 10. A countersink hole 26 through the cortex is also illustrated.

FIG. 5 illustrates the anchoring device 10 as it has been partially implanted through the pilot hole 25 into the cancellous portion of the bone. In some instances where the cortex is particularly thin, a pilot hole may be unnecessary. The soft tissue is attached to the anchoring device when the device is in position such as by suturing or wiring to the attachment head 15 of the anchoring device 10.

FIGS. 6 and 7 illustrate an instrument which can be used for the implantation of the anchor in accordance with the present invention.

Specifically, the instrument includes a central shaft 30 having a T-shaped handle 32 designed to allow the surgeon to easily grasp the handle 32 and rotate the shaft 30 to screw the anchor 10 into the bone through the optional pilot hole. The placement guide 34 includes a bottom surface 36 which can rest against the cortical surface where the anchor 10 is to be implanted. The guide 34 further includes an internal opening 38 having a diameter sufficient to receive the top portion of the anchor 10. The guide 34 further includes a bore 40 which provides a bearing surface for the shaft 30. At its lower end, the shaft 30 includes a head 42 having an internal slot 44 which receives the crossbar of the anchor 10 to enable the surgeon to apply torque to the anchor. The head 42 has an external diameter which cooperates with the internal diameter of the anchor 10. Optionally, the shaft 30 may also include a longitudinal, internal opening to receive a guide wire to allow for further cannulated surgical techniques.

During use of the anchor of the present invention, the attachment location is approached with standard surgical exposure. A pilot hole is drilled through the near cortex only and a drill sleeve is used to protect surrounding soft tissues. The hole consists of removal of cortex such that the head of the helix may be countersunk below the cortical surface. A tap, or a helical tool is fabricated from a material with a high modulus of elasticity, and that cuts the threads for the helix. The anchoring device 10 is inserted with an insertion tool such that the attachment head 15 is left out of the bone. The angle of insertion may be perpendicular to the bone surface or at a 45° angle. A suture may be passed under the exposed crossbar 17 of the attachment head 15 once or twice, depending on the surgeon's choice. The attachment tool is then used to countersink the attachment head 15 below bone level. The ligament or tendon is then sutured into place with a preferred suturing method such as Bunnell, whip, or modified Kessler. The wound is subsequently closed and the procedure is completed in standard fashion, or the head of the anchor may be used to attach the tissues without the use of structure.

FIGS. 8 through 12 show a second embodiment of the anchor 80 having a modular head 82 attached to a helix 84. The helix 84 engages the bone as shown in the earlier embodiments. This version rotates through 540° (1 full rotations) and terminates at one end in a three-sided point 86. At the other end, the helix 84 is formed into a ring 88 to form a seat for the head 82. The ring 88 may be a complete circle if it is welded together, or less than a circle, so long as it forms a good seat for the head 82. Preferably the ring 88 is the same diameter as the helix and the head 82 has the same outer diameter as the ring in order to allow the head to be countersunk into a plate or bone.

Figure 14:
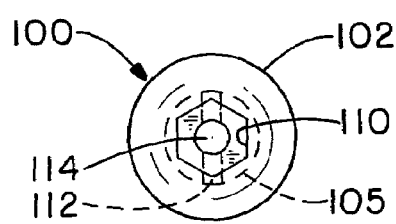
FIG. 14 is a top view of the embodiment shown in FIG. 13.
Figure 13:
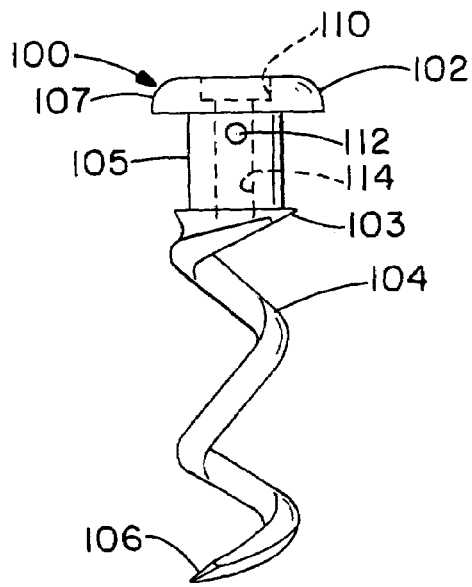
FIG. 13 is an elevational view of a third alternative embodiment of the invention.

Preferably both the head 82 and helix 84 are formed of implant-grade stainless steel (such as SS 22-13), or other biocompatible metals or polymers about 0.02 to 0.2 inch, and preferably from 0.05 to 0.1 inch from the top surface of the helix ring 88. The head 82 also includes an internal hex opening 90 to receive an anchor driver. The head 82 also includes a transverse through slot 92 shown in phantom in FIG. 9. The slot can be used to hold sutures in order to anchor tendons or ligaments. On the opposite side, the head 82 includes a necked area or stem 94 which is a constant diameter cylinder welded or otherwise adhered along the bottom edge to the ring 88. This may be fabricated from a solid piece of material. FIGS. 13 and 14 show a third embodiment of the anchor 100, having an integral head 102 which is formed as an integral continuation of the helical portion 104 of the anchor. The head 102 has a compound profile with a lower junction 103 between the helix and the head, a middle cylindrical body 105, and an upper enlarged button 107 that may fasten a suture or overlap a plate. Again, the helix 104 has a pointed insertion tip 106, and the elongate member which forms the helix may have a cutting surface formed by a triangular cross-section, or a buttress type thread. The head has a depth of from about 0.03 to about 0.25 inch, and includes a torque receiving recess, preferably an internal hexagon 110 which has a point to point measurement of about 0.15 to about 0.25 inch. Further, the head includes a through slot (or slots) 112 which can receive a suture. The head includes an internal through bore 114 for cannulated surgical techniques.

Figure 16:
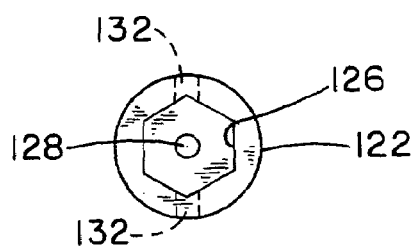
FIG. 16 is a top view of the embodiment shown in FIG. 15.
Figure 15:
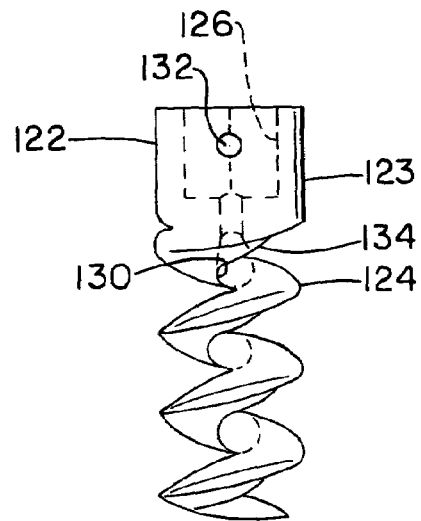
FIG. 15 is an elevational view of a fourth embodiment of the present invention.

FIGS. 15 and 16 show a fourth embodiment of the invention in which the head 122 is a cylindrical member 123 that extends from the helical member 124. The head 122 further includes an internal hexagonal torque driving recess 126 which may have a through bore 128 connection to the open upwardly tapering portion 130 of the helix 124. Through slots 132 may receive a suture. The taper 130 of the helix 124 results in a wedge shaped area 134 of the helix which is self-reinforcing for driving the helix into the bone. The blank is subsequently reamed using a conical auger, or a hot wire technique to form the tapering open helical structure of the present invention.

Figure 17:
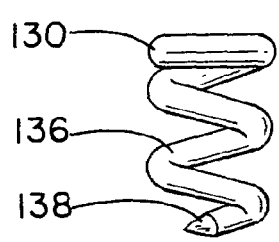
FIG. 17 is an elevational view of a fifth embodiment of the present invention.
Figure 18:
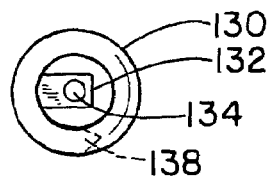
FIG. 18 is a top view of the embodiment of the invention shown in FIG. 17.
Figure 19:
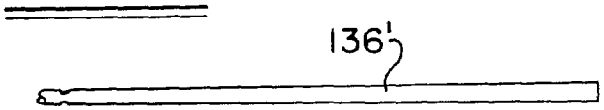
FIG. 19 illustrates an uncoiled filament which may be wound in a manner to comprise the embodiment shown in FIGS. 17–18.

FIGS. 17–19 represent a fifth embodiment of the helix 130 in accordance with the invention. The helix includes a cross bar 132 which has a bore 134 for cannulated techniques. The helix is made from a coiled filament 136 which can have a round cross-section or a thread-like cross section. The filament includes an insertion tip 138 and tapers along at least a part, and preferably all of its length by a slight amount, i.e. from 5 to 100% of the value of the diameter adjacent the insertion tip, and preferably from about 10 to about 50% of this value, and most preferably from about 15 to about 30% of this value.

EXAMPLE

Six samples of surgical-grade, stainless steel bone anchors in accordance with the invention were placed in a sample of artificial cancellous bone. Two samples each had a total longitudinal length of about 20 millimeters. The other four samples each had total lengths of about 13 millimeters. The other diameter of all samples was 5 millimeters and the wire diameter was 1.5 millimeters. Both long samples and two short samples had attachment heads which were crossbars and were attached by heliarc spot welding. The other short samples had crossbar attachment heads which were not welded.

Pullout tests were conducted using an MTS instrument. Straight, longitudinal pull was applied to the embedded anchors; this reproduced the least favorable condition for pullout characteristics. The results are shown in the table below. "Displacement" refers to bending of the crossbar in the longitudinal direction.

TABLE 1

| PLASTIC DEFORMATION | | |
|---|---|---|
| SHORT/NON-WELDED | SHORT/WELDED | LONG/WELDED |
| Average 48 lbs. with 2 millimeters of displacement | Average 52 lbs. with 2.2 millimeters of displacement | Average 58 lbs. with 2.4 millimeters of displacement |

All of the numbers represent desirable anchoring values.

While in accordance with the patent statutes the best mode and preferred embodiment have been set forth, the scope of the invention is not limited thereto, but rather by the scope of the attached claims.

What is claimed is:

1. A method of forming a tissue anchor which can be implanted using an insertion tool and comprising the steps of forming a blank member comprised of a one or more of stainless steel, titanium, polyglycolic acid, polylactic acid, or polydioxone hydroxyl apatite, having a external thread defining a major diameter which forms a helical structure comprised of an elongate member which spirals about a minor diameter, said helical structure having a length from about 3 millimeters to about 75 millimeters, an outer diameter of from about 1.5 to about 15 millimeters, a slope from about 0.5 to about 10 turns per centimeter and having at a first end, an insertion tip, and said blank having at a second end, an attachment head having an internal recess to receive the insertion tool, and subsequently forming a bore to eliminate the minor diameter in the blank so that the helical structure is open.

2. A method as set forth in claim 1 wherein said blank is formed by injection molding or on a screw machine.

3. A method as set forth in claim 2, wherein the bore in the helical structure has an internal diameter which tapers to a smaller diameter where the attachment head joins the helical structure.

4. A method as set forth in claim 3, wherein said bore is formed by reaming the blank.

5. A method as set forth in claim 1, wherein said attachment head has a cylindrical body.

6. A method as set forth in claim 1, wherein said attachment head further includes a portion having an enlarged outer diameter.

7. A method as set forth in claim 1 wherein the elongate member has a cross section dimension which tapers from the attachment head to the insertion tip and the increase in taper is from about 10 to about 50%.

8. A method as set forth in claim 7 wherein the elongate member has a cross section dimension which tapers from the attachment head to the insertion tip and the increase in taper is from about 15 to about 30%.

9. A method as set forth in claim 1 wherein the helical structure has from three to sixteen complete turns.

10. A method as set forth in claim 1 wherein the elongate member has a thread shaped cross-section.

11. A method as set forth in claim 1, wherein the elongated member tapers to decrease in diameter toward the insertion end.

12. A method of forming a tissue anchor which can be implanted using an insertion tool and comprising the steps of forming a blank member comprised of a one or more of stainless steel, titanium, polyglycolic acid, polylactic acid, or polydioxone hydroxyl apatite, having a external thread defining a major diameter which forms a helical structure comprised of an elongate member which spirals about a minor diameter, said helical structure having a length from about 3 millimeters to about 75 millimeters, an outer diameter of from about 1.5 to about 15 millimeters, a slope from about 0.5 to about 10 turns per centimeter and having at a first end, an insertion tip, and subsequently forming a bore to eliminate the minor diameter in the blank so that the helical structure is open.

13. A method as set forth in claim 12 wherein said blank is formed by injection molding or on a screw machine.

14. A method as set forth in claim 12, wherein the blank further has a second end including an attachment head and the bore in the helical structure has an internal diameter which tapers to a smaller diameter where the attachment head joins the helical structure.

15. A method as set forth in claim 14, wherein said bore is formed by reaming the blank.

16. A method as set forth in claim 14, wherein the attachment head has a cylindrical body.

17. A method as set forth in claim 14, wherein the attachment head further includes a portion having an enlarged outer diameter.

18. A method as set forth in claim 13 wherein the elongate member has a cross section dimension which tapers from the attachment head to the insertion tip and the increase in taper is from about 10 to about 50%.

19. A method as set forth in claim 13 wherein the elongate member has a cross section dimension which tapers from the attachment head to the insertion tip and the increase in taper is from about 10 to about 50%.

20. A method as set forth in claim 13 wherein the helical structure has from three to sixteen complete turns.

21. A method as set forth in claim 13 wherein the elongate member has a thread shaped cross-section.

* * * * *